(12) United States Patent
Cremins et al.

(10) Patent No.: US 9,279,750 B2
(45) Date of Patent: *Mar. 8, 2016

(54) METHOD AND COMPOSITION FOR STAINING AND SAMPLE PROCESSING

(71) Applicant: IRIS International, Inc., Chatsworth, CA (US)

(72) Inventors: Jack Cremins, Waterbury, CT (US); Carol Quon, Newbury Park, CA (US)

(73) Assignee: Iris International, Inc., Chatsworth, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/216,339

(22) Filed: Mar. 17, 2014

(65) Prior Publication Data

US 2014/0273081 A1  Sep. 18, 2014

Related U.S. Application Data

(60) Provisional application No. 61/799,152, filed on Mar. 15, 2013.

(51) Int. Cl.
*G01N 1/30* (2006.01)
*G01N 33/50* (2006.01)
*G01N 33/80* (2006.01)
*G01N 21/53* (2006.01)
*G01N 15/14* (2006.01)
*G01N 15/00* (2006.01)
*G01N 15/10* (2006.01)

(52) U.S. Cl.
CPC .............. *G01N 1/30* (2013.01); *G01N 15/1404* (2013.01); *G01N 15/147* (2013.01); *G01N 15/1434* (2013.01); *G01N 15/1463* (2013.01); *G01N 15/1468* (2013.01); *G01N 15/1475* (2013.01); *G01N 21/53* (2013.01); *G01N 33/5091* (2013.01); *G01N 33/5094* (2013.01); *G01N 33/80* (2013.01); *G01N 2015/0065* (2013.01); *G01N 2015/1037* (2013.01); *G01N 2015/1411* (2013.01); *G01N 2015/1413* (2013.01); *G01N 2015/1452* (2013.01); *G01N 2015/1486* (2013.01)

(58) Field of Classification Search
CPC ................................................... G01N 33/5094
See application file for complete search history.

(56) References Cited

U.S. PATENT DOCUMENTS

| 6,184,978 | B1 | 2/2001 | Kasdan et al. |
| 6,424,415 | B1 | 7/2002 | Kasdan et al. |
| 6,590,646 | B2 | 7/2003 | Kasdan et al. |
| 6,632,676 | B1 | 10/2003 | Crews et al. |
| 6,825,926 | B2 | 11/2004 | Turner et al. |
| 8,445,284 | B2 * | 5/2013 | Lapen et al. ............ 436/8 |
| 2007/0111276 | A1 | 5/2007 | Lefevre et al. |
| 2012/0322099 | A1 | 12/2012 | Lapen et al. |

FOREIGN PATENT DOCUMENTS

EP  0656540  6/1995

OTHER PUBLICATIONS

International Search Report and Written Opinion for Application No. PCT/US2014/030851 mailed Jul. 16, 2014.

* cited by examiner

*Primary Examiner* — Bin Shen
(74) *Attorney, Agent, or Firm* — Kilpatrick Townsend & Stockton LLP

(57) ABSTRACT

The present disclosure relates to a staining methodology employing a particle contrast agent composition capable of rapidly staining cells in a single step. The particle contrast agent composition can be comprised of a combination of one or more particle contrast agents, one or more permeabilizing agents, and one or more fixing agents. The particle contrast agent composition can include Crystal Violet, New Methylene Blue, Saponin, and Gluteraldehyde.

12 Claims, 10 Drawing Sheets

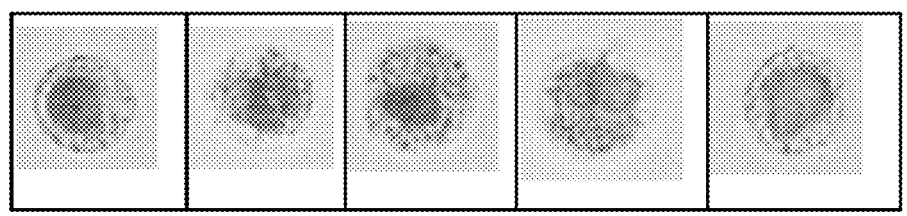
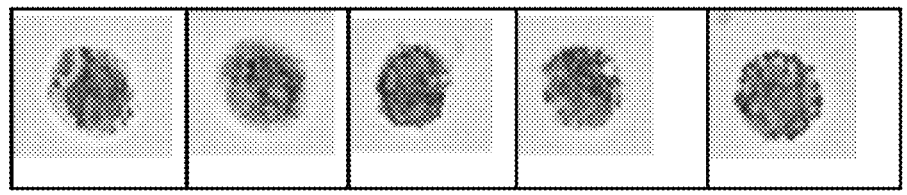
FIG. 7

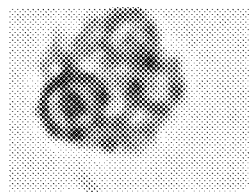
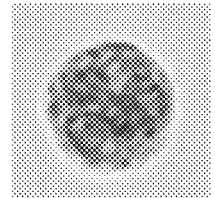
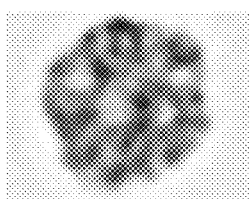
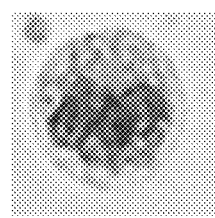
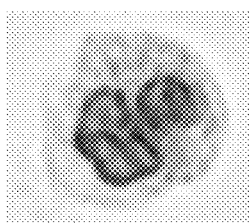
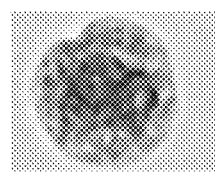
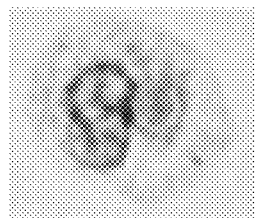
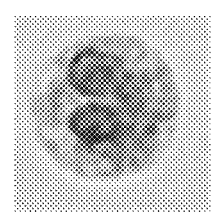
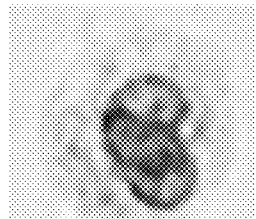
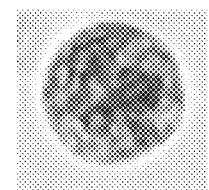
FIG. 8                    FIG. 9

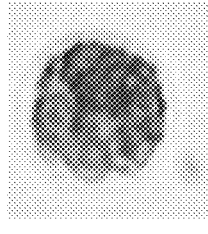
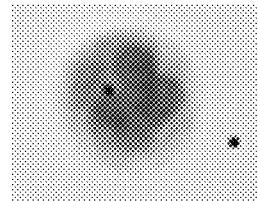
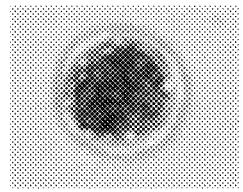
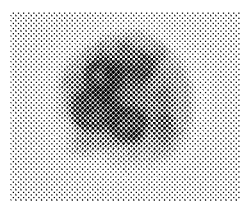
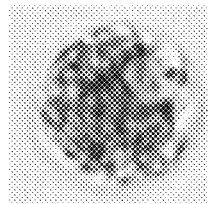
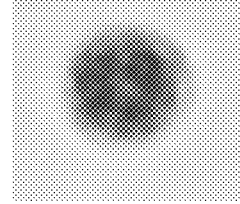
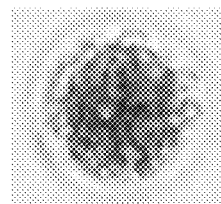
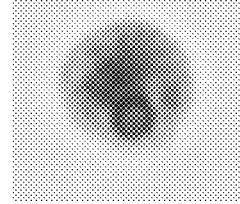
FIG. 10                    FIG. 11

METHOD AND COMPOSITION FOR STAINING AND SAMPLE PROCESSING

CROSS REFERENCE TO RELATED APPLICATIONS

The present application claims the benefit of U.S. Patent Application No. 61/799,152 filed Mar. 15, 2013, entitled "Analysis of Particles in Fluid Samples," which is hereby incorporated by reference in its entirety.

TECHNICAL FIELD

The present disclosure relates to particle contrast agents generally and more specifically to particle contrast agent compositions for use in wholly or partially automated devices to discriminate and quantify particles such as blood cells in a sample.

BACKGROUND

Blood cell analysis is one of the most commonly performed medical tests for providing an overview of a patient's health status. A blood sample can be drawn from a patient's body and stored in a test tube containing an anticoagulant to prevent clotting. A whole blood sample normally comprises three major classes of blood cells including red blood cells (erythrocytes), white blood cells (leukocytes) and platelets (thrombocytes). Each class can be further divided into subclasses of members. For example, five major types or subclasses of white blood cells (WBCs) have different shapes and functions. White blood cells may include neutrophils, lymphocytes, monocytes, eosinophils, and basophils. There are also subclasses of the red blood cell types. The appearances of particles in a sample may differ according to pathological conditions, cell maturity and other causes. Red blood cell subclasses may include reticulocytes and nucleated red blood cells.

A blood cell count estimating the concentration of RBCs, WBCs or platelets can be done manually or using an automatic analyzer. When blood cell counts are done manually, a drop of blood is applied to a microscope slide as a thin smear. Traditionally, manual examination of a dried, stained smear of blood on a microscope slide has been used to determine the number or relative amounts of the five types of white blood cells. Histological dyes and stains have been used to stain cells or cellular structures. For example, Wright's stain is a histologic stain that has been used to stain blood smears for examination under a light microscope. Staining a sample involves the use of multiple solutions and steps in proper order to ensure the staining agent is correctly applied and the cell structure is appropriately preserved. A fixing agent can be applied to the sample in a first step to preserve the sample from degredation and maintain the cell structure. Afterwards, a permeabilizing agent can be applied to the sample in a second step to dissolve cell membranes in order to allow the staining agent to enter the cells. The staining agent can be applied to the sample in a third step to stain the appropriate structures. The sample may be further rinsed for observation, or additional steps may be taken to apply additional stains, counterstains, or other perform other actions.

It is important to perform the steps in the appropriate order for the appropriate amounts of time. If the sample is permeabilized before being fixed, the cell structures in the sample can be degraded prior to being fixed and any ability to discern the original cellular morphology is lost. Additionally, the staining cannot occur prior to the permeabilizing step, or the staining agent will not properly penetrate the cells and stain the structures within the cells. Additionally, if any of the steps, such as fixing, permeabilizing, and staining, are performed too rapidly, the cell's morpohology may be lost and/or the cell and its internal structures may not be properly stained. Current staining techniques require multiple steps and significant time.

Current staining techniques require dilution of samples in the contrast agents generally around 1:500 or 1:5000. Thus, proper staining under current staining techniques result in Automated analyzers are becoming more prevalent. A Complete Blood Count (CBC) can be obtained using an automated analyzer, one type of which counts the number of different particles or cells in a blood sample based on impedance or dynamic light scattering as the particles or cells pass through a sensing area along a small tube. The automated CBC can employ instruments or methods to differentiate between different types of cells that include RBCs, WBCs and platelets (PLTs), which can be counted separately. For example, a counting technique requiring a minimum particle size or volume might be used to count only large cells. Certain cells such as abnormal cells in the blood may not be counted or identified correctly. Small cells that adhere to one another may be erroneously counted as a large cell. When erroneous counts are suspected, manual review of the instrument's results may be required to verify and identify cells.

Automated blood cell counting techniques can involve flow cytometry. Flow cytometry involves providing a narrow flow path, and sensing and counting the passage of individual blood cells. Flow cytometry methods have been used to detect particles suspended in a fluid, such as cells in a blood sample, and to analyze the particles as to particle type, dimension, and volume distribution so as to infer the concentration of the respective particle type or particle volume in the blood sample. Examples of suitable methods for analyzing particles suspended in a fluid include sedimentation, microscopic characterization, counting based on impedance, and dynamic light scattering. These tools are subject to testing errors. On the other hand, accurate characterization of types and concentration of particles may be critical in applications such as medical diagnosis.

In counting techniques based on imaging, pixel data images of a prepared sample that may be passing through a viewing area are captured using a microscopy objective lens coupled to a digital camera. The pixel image data can be analyzed using data processing techniques, and also displayed on a monitor.

Aspects of automated diagnosis systems with flowcells are disclosed in U.S. Pat. No. 6,825,926 to Turner et al. and in U.S. Pat. Nos. 6,184,978; 6,424,415; and 6,590,646, all to Kasdan et al., which are hereby incorporated by reference as if set forth fully herein.

Automated systems using dynamic light scattering or impedance have been used to obtain a complete blood count (CBC): total white blood cell count (WBC), total cellular volume of red blood cells (RBC distribution), hemoglobin HGB (the amount of hemoglobin in the blood); mean cell volume (MCV) (mean volume of the red cells); MPV (mean PLT volume); hematocrit (HCT); MCH (HGB/RBC) (the average amount of hemoglobin per red blood cell); and MCHC (HGB/HCT) (the average concentration of hemoglobin in the cells). Automated or partially automated processes have been used to facilitate white blood cell five part differential counting and blood sample analyses.

The various automated systems described above rely on rapid analysis of samples. The number of and duration of the steps of the staining process can be a limiting factor in the speed and efficacy of automated particle analysis systems. Automated particle analysis systems can be more efficient if the staining process is shortened, and further more efficient if the staining process is performed in a single step. Additionally, the automated particle analysis systems can be more efficient if the total size of the sample is kept to a minimum.

SUMMARY

A particle contrast agent composition is disclosed for staining a blood fluid sample being imaged in an automated particle analysis system. The particle contrast agent composition can include at least one particle contrast agent selected from the group consisting of Crystal Violet, New Methylene Blue, Methyl Green, Eosin Y, and Safranin O. The particle contrast agent composition can further include a permeabilizing agent selected from the group consisting of a surfactant, a saponin, a quarternary ammonium salt, a nonionic surfactant, a detergent; and a zwitterionic surfactant. The particle contrast agent composition can further include a fixing agent selected from the group consisting of gluteraldehyde and formaldehyde.

In one embodiment, the permeabilizing agent can be saponin present in amounts sufficient to result in concentrations between about 50 mg/L and about 750 mg/L under staining conditions. The fixing agent can be gluteraldehyde present in amounts sufficient to result in concentrations at or below 0.1% under staining conditions.

In one embodiment, the at least one particle contrast agent can include Crystal Violet, New Methylene Blue, and Eosin-Y. The ratio of the Crystal Violet to the New Methylene Blue can be between about 1:90 to about 1:110 under staining conditions. The Eosin-Y can be present in amounts sufficient to result in concentrations of about 3 μM to about 300 μM under staining conditions.

In one embodiment, the Crystal Violet can be present in amounts sufficient to result in concentrations of about 6 μM to about 10 μM under staining conditions. The New Methylene Blue can be present in amounts sufficient to result in concentrations of about 70 μM to about 2.4 mM under staining conditions. The Eosin-Y can be present in amounts sufficient to result in concentrations of about 10 μM to about 50 μM under staining conditions.

In some embodiments, the Crystal Violet is approximately 90% pure or greater. The New Methylene Blue can be approximately 70% pure or greater. The Eosin-Y can be approximately 80% pure or greater.

In some embodiments, the Crystal Violet is present in amounts sufficient to result in concentrations of about 7.8 μM under staining conditions. The New Methylene Blue is present in amounts sufficient to result in concentrations of about 735 μM under staining conditions. The Eosin-Y can be present in amounts sufficient to result in concentrations of about 27 μM under staining conditions. In some embodiments, the particle contrast agent composition can additionally include buffer components.

A method is disclosed for treating particles of a blood fluid sample which will be imaged using an automated particle analysis system. The method can include combining the blood fluid sample with a particle contrast agent composition to obtain a sample mixture and incubating the sample mixture at a temperature between about 37° Celsius and about 60° Celsius for fewer than 90 seconds. The particle contrast agent composition include at least one particle contrast agent selected from the group consisting of Crystal Violet, New Methylene Blue, Methyl Green, Eosin Y, and Safranin O; a permeabilizing agent selected from the group consisting of a surfactant, a saponin, a quarternary ammonium salt, a nonionic surfactant, a detergent; and a zwitterionic surfactant; and a fixing agent selected from the group consisting of gluteraldehyde and formaldehyde.

In some embodiments, the particle contrast agent can include Crystal Violet New Methylene Blue in amounts sufficient to result in a ratio of the Crystal Violet to the New Methylene Blue between about 1:1 to about 1:500 under staining conditions. The saponin can be included in amounts sufficient to result in concentrations between about 50 mg/L and about 750 mg/L under staining conditions. The gluteraldehyde can be included in amounts sufficient to result in concentrations at or below 0.1% under staining conditions. The method can include the sample mixture being incubated for fewer than 60 seconds.

In some embodiments, the particle contrast agent composition can include Crystal Violet present in amounts sufficient to result in concentrations at about 6 μM to about 10 μM under staining conditions. The New Methylene Blue can be present in amounts sufficient to result in concentrations of about 70 μM to about 2.4 mM under staining conditions. The Eosin-Y can be present in amounts sufficient to result in concentrations of about 10 μM to about 50 μM under staining conditions. The blood fluid sample can be combined with the particle contrast agent composition at a ratio of the blood fluid sample to the particle contrast agent composition of about 1:2 to about 1:10.

In some embodiments, the method can include heating the sample mixture to between 46° C. and about 49° C. for between 40 and 50 seconds.

In some embodiment, the Crystal Violet can be approximately 90% pure or greater. The New Methylene Blue can be approximately 70% pure or greater. The Eosin-Y can be approximately 80% pure or greater.

In some embodiments, the particle contrast agent can include Crystal Violet present in amounts sufficient to result in concentrations at about 7.8 μM under staining conditions; New Methylene Blue present in amounts sufficient to result in concentrations of about 735 μM under staining conditions; and Eosin-Y present in amounts sufficient to result in concentrations of about 27 μM under staining conditions. The particle contrast agent composition can further include buffer components. The blood fluid sample can be combined with the particle contrast agent composition at a ratio of the blood fluid sample to the particle contrast agent composition of about 1:3 to about 1:4. The sample mixture can be heated to about 47° C. for about 45 seconds.

The above described and many other features and attendant advantages of embodiments of the present invention will become apparent and further understood by reference to the following detailed description when considered in conjunction with the accompanying drawings.

BRIEF DESCRIPTION OF THE DRAWINGS

The specification makes reference to the following appended figures, in which use of like reference numerals in different figures is intended to illustrate like or analogous components

FIG. 7 is a representative illustration of stained cells according to an early Example 2.

FIG. 8 is a representative illustration of stained cells according to an early Example 3.

FIG. 9 is a representative illustration of stained cells according to an early Example 4.

FIG. 10 is a representative illustration of stained cells according to an early example.

FIG. 11 is a representative illustration of stained cells according to an early Example 5.

DETAILED DESCRIPTION

Figure 1:
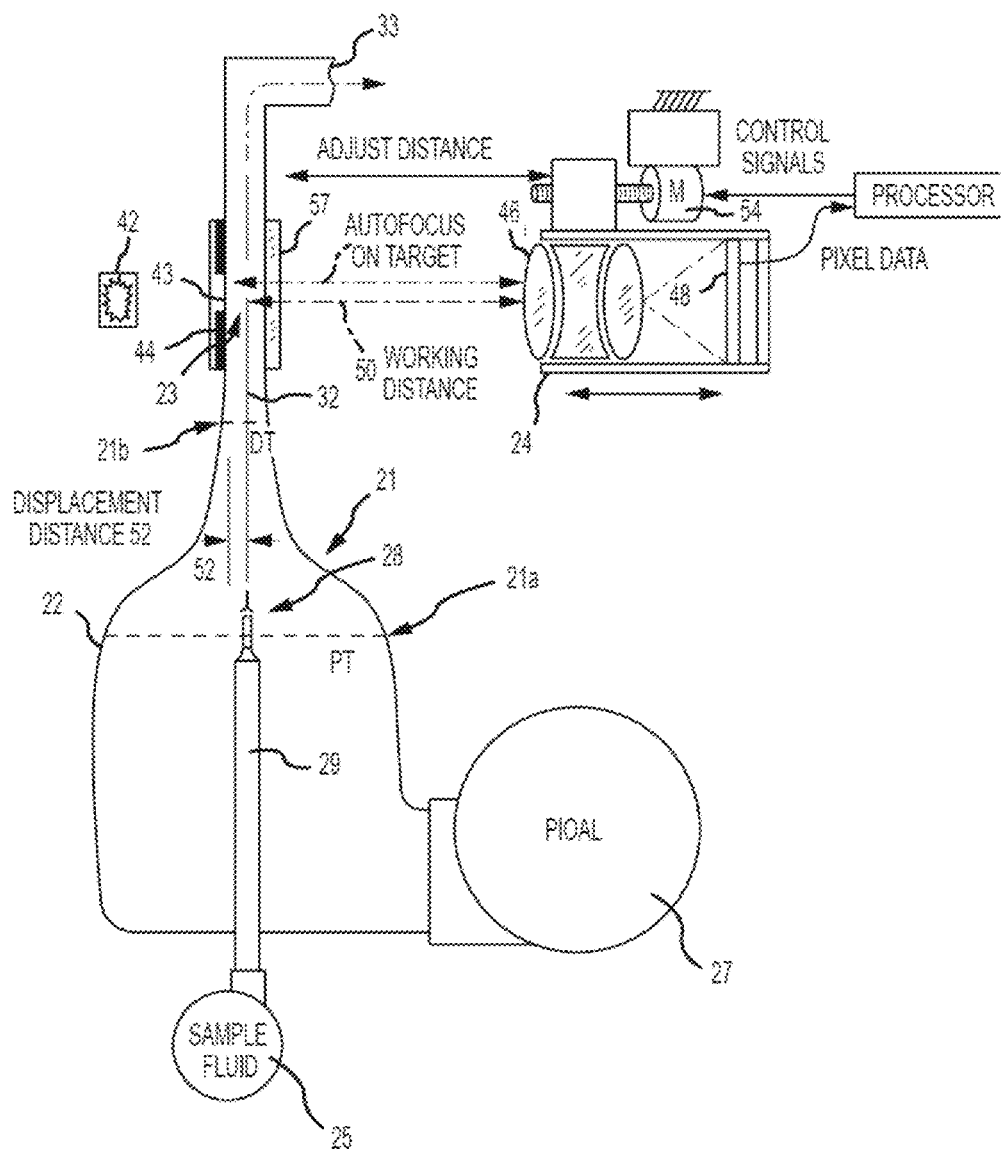
FIG. 1 is a schematic diagram of a flowcell for conveying a sample fluid according to one embodiment.

The present disclosure relates to a surprising and unexpected particle contrast agent composition for rapidly generating visual distinctions in a sample. The particle contrast agent composition can be especially useful in automated flow cytometry systems. The particle contrast agent composition is comprised of a combination of a particle contrast agent, a permeabilizing agent, and a fixing agent. In one embodiments, the particle contrast agent composition is a mixture of Crystal Violet, New Methylene Blue, Saponin, and Gluteraldehyde. In an embodiment that is surprisingly effective, under staining condutions, the Crystal Violet is present in amounts sufficient to result in concentrations of about 7.8 µM, the New Methylene Blue is present in amounts sufficient to result in concentrations of about 735 µM, the Saponin is present in amounts sufficient to result in concentrations between about 50 mg/L and about 750 mg/L, the composition further includes Eosin-Y present in amounts sufficient to result in concentrations of about 27 µM, and the Gluteraldehyde is present in amounts sufficient to result in concentrations at or below 0.1%.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may be drawn not to scale.

The particle contrast agent composition of the invention, when applied to a blood fluid sample, causes the staining of cells in such sample similar to that of a blood smear treated with a standard blood smear stain, and in particular similar to a blood smear stain with Wright's stain. Wright's stain is a histologic stain that facilitates the differentiation of blood cell types (e.g. WBC). It is used primarily to stain peripheral blood smears and bone marrow aspirates which are examined under a light microscope. In cytogenetics it is used to stain chromosomes to facilitate diagnosis of syndromes and diseases. There are related stains known as the buffered Wright stain, the Wright-Giemsa stain, and the buffered Wright-Giemsa stain. Because the Wright's stain process involves alcohol solvent, this staining procedure is destructive to viable cells and does not result in substantially intact cells. The May-Grünwald stain, which produces a more intense coloration, also takes a longer time to perform.

Aspects and embodiments of the present invention are based on the surprising and unexpected discovery that certain particle contrast agent compositions, including for example, stain/dye compositions, and/or combinations thereof, have unexpected properties and efficacy when used to perform automated, image-based sample analysis, such as blood analysis.

Hematology—Particle Analysis System

The compositions and method disclosed herein can be used with many different types of hematology imaging systems. In particular, the compositions and methods described herein can be used with image-based sample analysis, such as flow-cell analysis. An example of such a flowcell analysis can include traditional, known methods of flow cytometry. Additionally, the compositions and methods described herein can be advantageously used with the flowcell analysis systems and methods described in brief detail below and described further in the co-filed applications entitled "Flowcell Systems And Methods For Particle Analysis In Blood Samples," application Ser. No. 14/216,533, filed Mar. 17, 2014, and "Hematology Systems and Methods," Application No. PCT/US2014/030942, filed Mar. 18, 2014, both of which are hereby incorporated by reference.

FIG. 1 is a schematic representation of an exemplary flowcell 22 for conveying a sample fluid (e.g., the sample mixture described below) through a viewing zone 23 of a high optical resolution imaging device 24 in a configuration for imaging microscopic particles in a sample flow stream 32 using digital image processing. Flowcell 22 is coupled to a source 25 of sample fluid which may have been subjected to processing, such as contact with a particle contrast agent composition as described in further detail below. Flowcell 22 is also coupled to one or more sources 27 of a particle and/or intracellular organelle alignment liquid (PIOAL), such as a clear glycerol solution having a viscosity that is greater than the viscosity of the sample fluid.

The sample fluid is injected through a flattened opening at a distal end 28 of a sample feed tube 29, and into the interior of the flowcell 22 at a point where the PIOAL flow has been substantially established resulting in a stable and symmetric laminar flow of the PIOAL above and below (or on opposing sides of) the ribbon-shaped sample stream. The sample and PIOAL streams may be supplied by precision metering pumps that move the PIOAL with the injected sample fluid along a flowpath that narrows substantially. The PIOAL envelopes and compresses the sample fluid in the zone 21 where the flowpath narrows. Hence, the decrease in flowpath thickness at zone 21 can contribute to a geometric focusing of the sample stream 32. The sample fluid ribbon 32 is enveloped and carried along with the PIOAL downstream of the narrowing zone 21, passing in front of, or otherwise through the viewing zone 23 of, the high optical resolution imaging device 24 where images are collected, for example, using a CCD. The sample fluid ribbon flows together with the PIOAL to a discharge 33.

As shown here, the narrowing zone 21 can have a proximal flowpath portion 21a having a proximal thickness PT and a distal flowpath portion 21b having a distal thickness DT, such that distal thickness DT is less than proximal thickness PT. The sample fluid can therefore be injected through the distal end 28 of sample tube 29 at a location that is distal to the proximal portion 21a and proximal to the distal portion 21b. Hence, the sample fluid can enter the PIOAL envelope as the PIOAL stream is compressed by the zone 21. wherein the sample fluid injection tube has a distal exit port through which sample fluid is injected into flowing sheath fluid, the distal exit port bounded by the decrease in flowpath size of the flowcell.

The digital high optical resolution imaging device 24 with objective lens 46 is directed along an optical axis that intersects the ribbon-shaped sample stream 32. The relative distance between the objective 46 and the flowcell 33 is variable by operation of a motor drive 54, for resolving and collecting a focused digitized image on a photosensor array.

Particle Contrast Agent Composition

Figure 2:
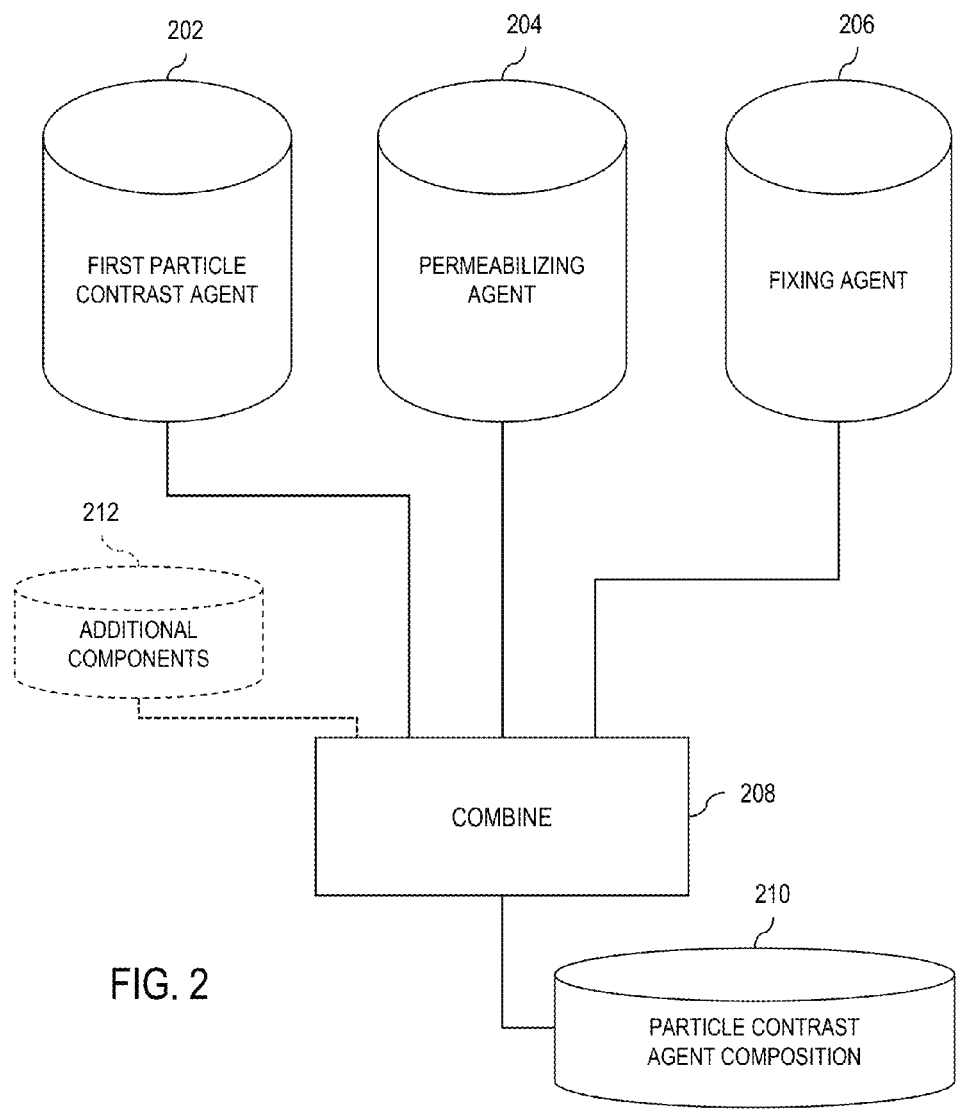
FIG. 2 is a schematic diagram of the preparation of a particle contrast agent composition according to one embodiment.

FIG. 2 is a schematic diagram of the preparation of a particle contrast agent composition according to one embodiment. At block 208, a particle contrast agent 202, a permeabilizing agent 204, and a fixing agent 206 are combined to create the particle contrast agent composition 210. In one embodiment, the particle contrast agent 202, permeabilizing agent 204, and fixing agent 206 are combined at the same time. In other embodiments, one of the particle contrast agent 202, permeabilizing agent 204, and fixing agent 206 is combined with another one of the particle contrast agent 202, permeabilizing agent 204, and fixing agent 206, which is then combined with the last of the particle contrast agent 202, permeabilizing agent 204, and fixing agent 206, in any order. The combination at block 208 can be performed in any order and in any suitable way.

In alternate embodiments, one of the permeabilizing agent 204 and fixing agent 206 is not included in the particle contrast agent composition 210. In still further embodiments, additional materials are combined at block 208 as part of the particle contrast agent composition 210, as described in further detail below.

The particle contrast agent composition 210 can be provided as part of a kit. The particle contrast agent composition 210 can be provided already prepared or as one or more components that must be combined.

Particle Contrast Agent

The particle contrast agent 202 can be any contrast agent capable of producing visible distinctions, such as those similar to a Wright stain. Examples of such contrast agents include Alcian Blue and Alcian Blue 86 (PAS neutral and acidic mucosubstances); Alizarin Red S; Allura Red AC (azodye red dye#40); Analine Blue (cilia intensified with oxalic acid); Auramine O; Azure B; Azure C; Bismarck Brown; Brilliant Blue FCF (Comassie blue); Brilliant cresyl blue; Brilliant green; Carmium (red nuclear dye composed of Carminic acid and Potassium alum); Congo red; Chlorozol black E (nuclei black, cyto gray, glycogen pink); Cresyl violet acetate; Darrow red; Eosin bluish; Erythrosin B (red dye #3); Ethyl eosin; Fast Green FCF (green dye#3); Fuchin basic—(nuclei and flagella); Fluorescein-(Mercurochrome); Giemsa-peripheral blood smears; Harris hematoxylin-regressive nuclear stain; Indigo Carmine (Blue dye#2); Janus Green B (mitochondria); Jenner Stain—(peripheral blood smears); Light Green SF yellowish; MacNeal—(tetrachrome blood stain); Malachite green; Methyl orange; Martius yellow; Mayer's Hematoxylin-progressive nuclear stain; Methyl violet 2B; Methenamine Silver-Peroidic acid; Methylene violet; May Grunwald-hematological stain; MTT—formazan stain; Mucicarmine—primary tumor stain; Neutral red; Nigrosin; Nile Blue A; Nuclear Fast red C.I. 60760; Napthal AS; Nitro-Blue Tetrazolium-fast formazan dye; Orange G; Orange II; Orcein; Papanicolaou Stain EAS—brilliant cytoplasmic staining; Pararosanilin; Pararosanaline; Periodic Acid Schiff-(PAS, specific carbohydrate stain); Phyloxine B; Protargol S; Pyronin B; Pyronin Y; Resazurin; Romanowsky-Giemsa; Rose Bengal; Safranin O; Sudan Black B; Sudan III—(with alpha-napthol stains myeloid granules); Sudan IV—stains triglycerides; Tartrazine—(azo dye Yellow#5); Thionin—stains meta chromatin; Triphenyl Tetrazolium; TTC—Formazan red dye; Toluidine Blue O; Wright's Stain—(fixative, buffer and stain for conventional blood smears); and Wright Giemsa.

Through non-trivial efforts and experimentation, it has been found that surprisingly effective results can be achieved in the particle contrast agent composition 210, as described in further detail herein, with the use of a particle contrast agent 202 that includes at least one of Crystal Violet, New Methylene Blue, Safranin O, Eosin Y and Methyl Green. The particle contrast agent 202 is added in an amount effective to stain viable and/or substantially intact cells for image-based categorization and subcategorization. The particle contrast agent 202 can be any combination of two or more of the aforementioned particle contrast agents. The particle contrast agent 202 can be selected to efficaciously obtain "Wright-like" stained images of vital and/or substantially intact cells.

In one embodiment, the particle contrast agent 202 includes Crystal Violet. The Crystal Violet can be present in amounts sufficient to achieve between about 1 $\mu$M to about 100 $\mu$M under staining conditions. As used herein, the term "under staining conditions" refers to when the component is mixed with the sample. The Crystal Violet can be present in amounts sufficient to achieve between about 6 $\mu$M to about 10 $\mu$M under staining conditions. The Crystal Violet can be present in amounts sufficient to achieve about 7.8 $\mu$M under staining conditions. The Crystal Violet can be present in amounts sufficient to achieve very nearly 7.8 $\mu$M under staining conditions. The Crystal Violet can be purified to at least 90% pure. The Crystal Violet can be purified to at least 91%, 92%, 93%, 94%, 95%, 96%, 97%, or 98% pure. The Crystal Violet can be purified to at least 99% pure. The particle contrast agent 202 can be solely Crystal Violet, or can be Crystal Violet combined with one or more additional particle contrast agents.

In one embodiment, the particle contrast agent 202 includes New Methylene Blue. The New Methylene Blue can be present in amounts sufficient to achieve between about 70 $\mu$M to about 2.4 mM under staining conditions. The New Methylene Blue can be present in amounts sufficient to achieve between about 500 $\mu$M to about 950 $\mu$M under staining conditions. The New Methylene Blue can be present in amounts sufficient to achieve about 735 $\mu$M under staining conditions. The New Methylene Blue can be present in amounts sufficient to achieve very nearly 735 $\mu$M under staining conditions. The New Methylene Blue can be purified to at least 70% pure. The New Methylene Blue can be purified to at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% pure. The New Methylene Blue can be purified to at least 100% pure.

In some embodiments, surprisingly effective results are achieved when the particle contrast agent 202 includes both Crystal Violet and New Methylene Blue. The ratio of Crystal Violet to New Methylene Blue can be between about 1:1 to about 1:500 (molar/molar). The ratio of Crystal Violet to New Methylene Blue can be between about 1:50 to about 1:160 (molar/molar). The ratio of Crystal Violet to New Methylene Blue can be between about 1:90 to about 1:110 (molar/molar).

In one embodiment, the particle contrast agent 202 includes Eosin Y. The Eosin Y can be present in amounts sufficient to achieve between about 3 $\mu$M to about 300 $\mu$M under staining conditions. The Eosin Y can be present in amounts sufficient to achieve between about 10 µM to about 50 µM under staining conditions. The Eosin Y can be present in amounts sufficient to achieve about 27 µM under staining conditions. The Eosin Y can be present in amounts sufficient to achieve very nearly 27 µM under staining conditions. The Eosin Y can be purified to at least 80% pure. The Eosin Y can be purified to at least 81%, 82%, 83%, 84%, 85%, 86%, 87%, 88%, 89%, 90%, 91%, 92%, 93%, 94%, 95%, 96%, 97%, 98%, or 99% pure. The Eosin Y can be purified to at least 100% pure.

In some embodiments, surprisingly effective results are achieved when the particle contrast agent 202 is a combination of Crystal Violet, New Methylene Blue, and Eosin Y, each having any combination of concentrations and purities as described above. In some embodiments, the particle contrast agent 202 is specifically Crystal Violet present in amounts sufficient to achieve about 7.8 µM, New Methylene Blue present in amounts sufficient to achieve about 735 µM, and Eosin Y present in amounts sufficient to achieve about 27 µM. In some embodiments, the particle contrast agent 202 is specifically at least 99% pure Crystal Violet present in amounts sufficient to achieve about 7.8 µM, at least 99% pure New Methylene Blue present in amounts sufficient to achieve about 735 µM, and at least 99% pure Eosin Y present in amounts sufficient to achieve about 27 µM.

In one embodiment, the particle contrast agent 202 includes Safranin O. The Safranin O can be present in amounts sufficient to achieve between about 1 µM to about 100 µM under staining conditions. The Safranin O can be present in amounts sufficient to achieve between about 3 µM to about 30 µM under staining conditions. The Safranin O can be present in amounts sufficient to achieve about 9 µM under staining conditions. The Safranin O can be present in amounts sufficient to achieve very nearly 9 µM under staining conditions. The Safranin O can be purified to at least 80% pure. The Safranin O can be purified to at least 81%, 82%, 83%, 84%, 85%, 86%, 87%, 88%, 89%, 90%, 91%, 92%, 93%, 94%, 95%, 96%, 97%, 98%, or 99% pure. The Safranin O can be purified to at least 100% pure.

In one embodiment, the particle contrast agent 202 includes Methyl Green. The Methyl Green can be present in amounts sufficient to achieve about 0.1 g/L under staining conditions. The Methyl Green can be present in amounts sufficient to achieve very nearly 0.1 g/L under staining conditions. The Methyl Green can be purified to at least 80% pure. The Methyl Green can be purified to at least 81%, 82%, 83%, 84%, 85%, 86%, 87%, 88%, 89%, 90%, 91%, 92%, 93%, 94%, 95%, 96%, 97%, 98%, or 99% pure. The Methyl Green can be purified to at least 100% pure.

In some embodiments, the particle contrast agent 202 includes one or more of Crystal Violet, New Methylene Blue, Safranin O, Eosin Y and Methyl Green in amounts effective to generate visual distinctions in particles, for example, by enhancing intracellular content features of particles in a sample when presented for imaging. The particle contrast agent 202 can be present in amounts sufficient to enhance and/or stain subcellular structures of neutrophils, lymphocytes, monocytes, eosinophils, and basophils as well as reticulocytes, nucleated red blood cells, platelets, blast, promyelocyte, myelocyte, metamyelocyte, or cell fragments. Visualizable or visual distinctions can include any particle or intraparticle features that may be visualizable or otherwise detectable using any light source (e.g., UV, visible, IR).

In embodiments where the particle contrast agent composition 210 includes two or more particle contrast agents 202, the amounts of each of the particle contrast agents 202 can be adjusted appropriately, depending on whether the particle contrast agents 202 have independent, competitive and/or enhancing effects on the generation of visual distinctions for particle categorization and subcategorization.

Permeabilizing Agent

In some embodiments, the permeabilizing agent 204 can include a surfactant. In some embodiments, the permeabilizing agent 204 can include a saponin. In alternate embodiments, the permeabilizing agent 204 can include at least one of a quarternary ammonium salt, a nonionic surfactant, and a zwitterionic surfactant. The permeabilizing agent can alter the permeability of a cell in order to increase accessibility of the particle contrast agent 202 to the intracellular contents. The permeabilizing agent can be selected and included in quantities sufficient to permit a rapid, one-step staining procedure.

Examples of a nonionic surfactant can include (1) polyoxyethylene alkyl or aryl ethers (polyethoxylates), including straight-chain aliphatic hydrophobes etherified to polyethylene glycol or polyoxyethylene ethanol, e.g., Brij® 35; (2) branched-chain aliphatic/aromatic (e.g., octylphenol) hydrophobes etherified to polyethylene glycol, e.g., Triton X®-100; (3) straight-chain aliphatic/aromatic (e.g., n-nonylphenol) hydrophobes etherified to polyethylene glycol, e.g., Igepal® C0897; and (4) straight-chain aliphatic (e.g., carboxylic acid) hydrophobes esterified to polyethylene glycol, e.g., Myrj® 53, and others. Examples of nonionic polyoxyethylene alkyl or aryl ethers (polyethoxylates) surfactants can include polyoxyethylene(4) lauryl ether (Brij® 30); polyoxyethylene(23) lauryl ether (Brij® 35); polyoxyethylene(2) cetyl ether (Brij® 52); polyoxyethylene(20) cetyl ether (Brij® 58); polyoxyethylene(2) stearyl ether (Brij® 72); polyoxyethylene(10)stearyl ether (Brij® 76); polyoxyethylene(20) stearyl ether (Brij® 78); polyoxyethylene(2) oleyl ether (Brij® 92); polyoxyethylene(10) oleyl ether (Brij® 96); polyoxyethylene(20) oleyl ether (Brij® 98); polyoxyethylene (21) stearyl ether (Brij® 721); polyoxyethylene(100) stearyl ether (Brij® 700); and others. Further examples of nonionic surfactants can include Triton X®-100 (non-reduced or reduced), Triton®X-114 non-reduced or reduced), Triton X®-165, and Triton X®-305 (non-reduced and reduced), and others.

In an embodiment, the permeabilizing agent 204 can include Brij® 35 at amounts sufficient to result in concentrations of about 0.10 g/L to about 0.20 g/L under staining conditions. The Brij® 35 can be present in amounts sufficient to result in concentrations of about 0.10 g/L to about 0.16 g/L under staining conditions. The Brij® 35 can be present in amounts sufficient to result in concentrations of about 0.012 g/L to about 0.14 g/L.

Examples of zwitterionic surfactants can include TDAPS (tetradecyldimethylammoniopropanesulfonate), CHAPSO (3-[(3-cholamidopropyl) dimethylammonio]-2-hydroxy-1-propanesulfonate), alkyl N,N-dimethyl N-oxides having from about 12 to about 16 carbon atoms, lauryl dimethylamine N-oxide (LO), DDAPS(N-dodecyl-N,N-dimethyl-3-ammonio-1-propanesulfonate), and others.

In some embodiments, the permeabilizing agent 204 includes an agent sufficient to lyse red blood cells. In some embodiments, the permeabilizing agent 204 includes an agent sufficient to lyse red blood cells other than reticulocytes or nucleated red blood cells. In some embodiments, the permeabilizing agent 204 includes an agent sufficient to lyse red blood cells while white blood cells, reticulocytes, nucleated red blood cells, platelets, and other cells remain substantially intact. In some embodiments, the permeabilizing agent 204 renders the members and/or nuclear membranes of white blood cells, reticulocytes, nucleated red blood cells, and/or platelets more permeable and/or porous to facilitate access by the particle contrast agent 202.

In some embodiments, the permeabilizing agent 204 is selected to be able to quickly create the pores or openings necessary to allow the particle contrast agent 202 to enter cells in the sample.

Through non-trivial efforts and experimentation, it has been found that surprisingly effective results can be achieved in some embodiments of the particle contrast agent composition 210 with the use of a permeabilizing agent 204 that includes 5PD-Lytic available from Clinical Diagnostic Solutions (CDS) in Ft. Lauderdale, Fla. 5PD-Lytic includes saponin. 5PD-Lytic is generally described in U.S. Pat. No. 6,632,676, herein incorporated by reference.

Through non-trivial efforts and experimentation, it has been found that surprisingly effective results can be achieved in some embodiments of the particle contrast agent composition 210 with the use of a permeabilizing agent 204 includes a saponin present in amounts sufficient to result in concentrations of about 10 mg/L to about 1000 mg/L under staining conditions. In some embodiments, the saponin is present in amounts sufficient to result in concentrations of about 50 mg/L to about 750 mg/L. In some embodiments, the saponin can be a quarternary ammonium-substituted saponin ether.

Fixing Agent

In some embodiments, the fixing agent 206 can be selected to ensure the white blood cells do not degrade during staining and imaging. In some embodiments, the fixing agent 206 can ensure other cells and cell structures do not degrade. Examples of fixing agents can include glutaraldyde; formaldehyde; cross-linking agents; ammonia picrate in isotonic saline (e.g., for methylene blue staining); ethyl alcohol; methanol (e.g., at room temperature, −20° C. or −70° C.); Heidenhain's Susa—HgCl$_2$, NaCl Trichloroacetic acid, formalin; Bouin's—Picric acid, Formalin, acetic acid; Duboseq-Brazil—Bouins with 80% EtOH; Carnoy's—EtOH, Chloroform, acetic acid; Zenker's—HgC$_{12}$, K$_2$CrO$_7$, NaSO$_4$.H$_2$O; acetocarmine; Gatensby's—Chromic acid, Osmium tetroxide, NaCl; Baker's—Formalin, CaCl$_2$; Smith's—K$_2$Cr$_2$O$_7$, formalin, acetic acid; 1% methyl green, 1% acetic acid; Phenol, formalin, glycerol, Genetian violet; Schaudin—HgCl$_2$, EtOH, acetic acid; Champy's—Chromic acid, K$_2$CrO$_7$, OsO$_4$; Fleming's—Cromic acid, OsO4, acetic acid; Formol-Silver—Formaldehyde, AgNO$_3$; Streck's Tissue Fixative—Bronopol, Diazolidinyl urea, ZnSO$_4$.7H$_2$O, sodium citrate; 1% imidazolidnyl urea in PBS; Glyoxal: Glyofix, Prefer, Safefix, Histochoice; Glydant—Hydantoin; Dimethylol urea; Sodium hydroxymethylglycinate; Karnovsky's; Mecuric chloride (B-5); Hollande's; and others. In addition, suitable exemplary fixative can include any of the following either alone or in combination.

In some embodiments, the fixing agent 206 can be an oxidizing agent, a mercurial, a picrate, a hepes-glutamic acid buffer-mediated organic solvent protection effect (HOPE) fixative, or a water soluble preservative. Examples of oxidizing agents include Potassium dichromate, chromic acid, potassium permanganate, and others. Examples of mercurial include B-5, Zernker's fixative, and others. Examples of water-soluble preservatives include methyl paraben, propyl paraben, dimethylolurea, 2-pyridinethiol-1-oxide, sorbic acid, potassium sorbate, and others.

Through non-trivial efforts and experimentation, it has been found that surprisingly effective results can be achieved in some embodiments of the particle contrast agent composition 210 with the use of a fixing agent 206 that includes at least one of Gluteraldehyde and Formaldehyde.

In some embodiments, surprisingly effective results can be achieved by using a fixing agent 206 that includes Gluteraldehyde at or below 0.1% by weight.

Additional Components

In some embodiments, optional additional components 212 can be optionally combined at block 208 into the particle contrast agent composition 210. Examples of additional components 212 can include buffer components, viscosity modifying agents, an antimicrobial agent, an osmotic adjusting agent, an ionic strength modifier, a surfactant, a chelating agent, and others. In some embodiments, surprisingly effective results can be achieved when the particle contrast agent composition 210 includes a phosphate buffered saline.

Exemplary viscosity modifying agents include natural hydrocolloids (and derivatives), such as carrageenan, locust bean gum, guar gum, and gelatin; sugars (and derivatives), such as dextrose, fructose; polydextrose; dextrans; polydextrans; saccharides; and polysaccharides; semi-synthetic hydrocolloids (and derivatives), such as Methylcellulose, Carboxymethylcellulose; Synthetic hydro colloids (and derivatives), such as Carbopol®; and Clays (and derivatives), such as Bentonite and Veegum®.

Rapid, One-Step Staining Process

Figure 3:
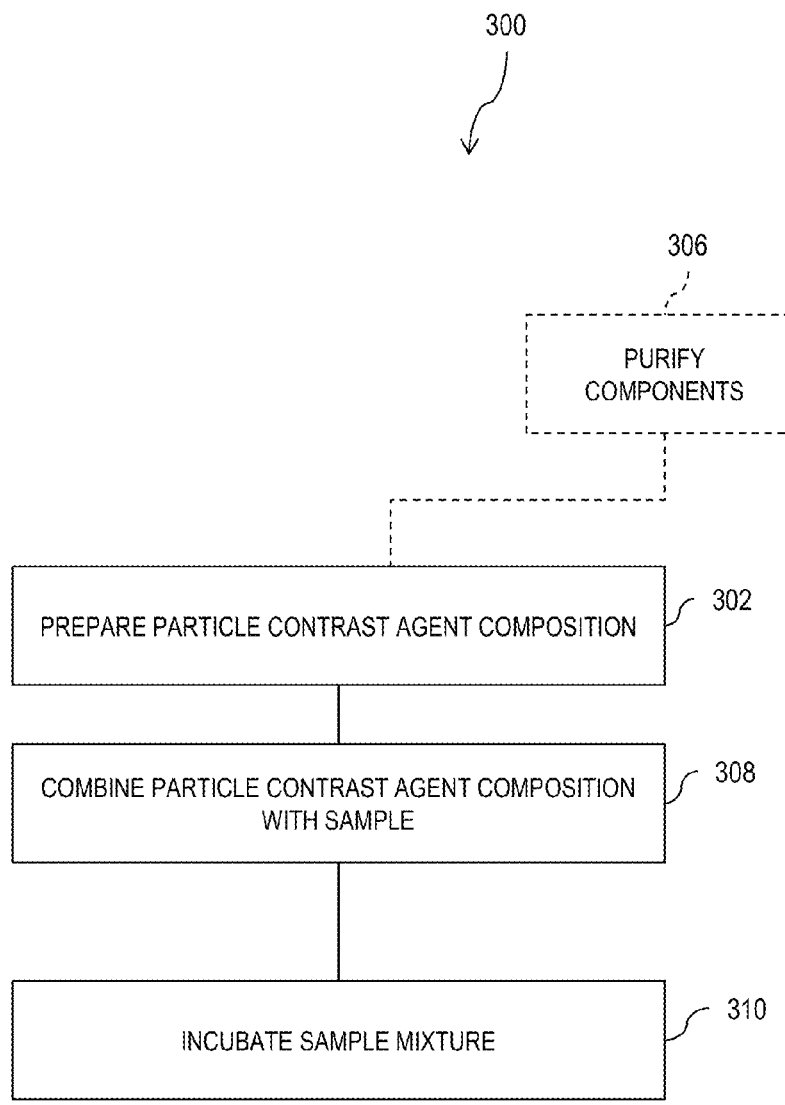
FIG. 3 is a flowchart of a rapid, one-step staining process according to one embodiment.

FIG. 3 is a flowchart of a rapid, one-step staining process 300 according to one embodiment. While the rapid, one-step staining process 300 can contain several sub-steps, the term "one-step" is used to identify that the sample need not be introduced to multiple, different solutions during the staining procedure. The particle contrast agent composition 210 is prepared at block 302, as described above with reference to FIG. 2. Optionally, in some embodiments, components, such as any particle contrast agents 202, can be purified at block 306. Purifying particle contrast agents 202 can reduce the level of precipitates formed upon contact with a sample, thereby reducing the background and improving the results of image-based blood sample analysis with a decreased need for further review of images or slides, or manually prepared microscopy.

At block 308, the particle contrast agent composition 210 is combined with the sample. The particle contrast agent composition 210 can be combined with the sample in any suitable way, including mixing together. Combining at block 308 can include diluting the sample with a certain amount of particle contrast agent composition 210. The sample can be diluted with particle contrast agent composition 210. The amount of dilution can be selected to provide an optimal number of cells per frame during an image-based analysis. The amount of dilution can be selected to provide an optimal number of white blood cells per frame during an image-based analysis. The amount of dilution can be otherwise selected to provide an optimal volume for any other non-image-based analysis.

Through non-trivial efforts and experimentation, it has been found that surprisingly effective results can be achieved in some embodiments of the particle contrast agent composition 210 with the use of a ratio of the particle contrast agent composition 210 to the sample at between about 2:1 to about 20:1. The ratio of the particle contrast agent composition 210 to the sample can be between about 3:1 to about 10:1. The ratio of the particle contrast agent composition 210 to the sample can be between about 3:1 to about 4:1. The ratio of the particle contrast agent composition 210 to the sample can be between about 3:1 or about 4:1. In some embodiments, surprisingly effective results can be achieved using a ratio of the particle contrast agent composition 210 to the sample at very nearly 3:1 or very nearly 4:1.

Surprisingly effective results can be achieved by using particle contrast agent with 40 mL of 5PD-Lytic and 50 mL of Phosphate Buffered Saline with a dilution ratio of 10:1 particle contrast agent composition 210 to sample. Surprisingly effective results can be achieved by using particle contrast agent with 40 mL of 5PD-Lytic, extra saponin, and 40 mL of Phosphate Buffered Saline with a dilution ratio of 5:1 particle contrast agent composition 210 to sample. Surprisingly effective results can be achieved by using particle contrast agent with 40 mL of 5PD-Lytic, extra saponin, and 36 mL of Phosphate Buffered Saline with a dilution ratio of 4:1 particle contrast agent composition 210 to sample.

In some embodiments, the sample is combined with the particle contrast agent composition 210 at elevated temperatures, such as any of the temperatures described below with reference to incubating.

As used herein, the combined sample and particle contrast agent composition 210 is referred to as the sample mixture.

At block 310, the sample mixture is incubated for a certain amount of time at a certain temperature. Incubation can increase the permeability of the cells or their internal structures, allowing the particle contrast agent 202 to better infiltrate the cells or cellular structures. The time and temperature of incubation can be selected to enable the particle contrast agent composition 210 to properly permeate, fix, and stain the sample. The time and temperature of incubation can be selected to ensure lysing of red blood cells while keeping white blood cells, platelets, and nucleated red blood cells substantially intact.

Through non-trivial efforts and experimentation, it has been found that surprisingly effective results can be achieved in some embodiments of the particle contrast agent composition 210 with incubation of the sample mixture at temperatures between about 37° C. and about 60° C. for about 1 to 60 seconds. The sample mixture can be heated to temperatures between about 46° C. and about 49° C. The sample mixture can be incubated for between 40 and 50 seconds. The sample mixture can be incubated up to an hour. In some embodiments, surprisingly effective results can be achieved by incubating the sample mixture at about 48° C. for about 45 seconds. In some embodiments, surprisingly effective results can be achieved by incubating the sample mixture at about 47° C. for about 45 seconds.

In some embodiments, the combining at block 308 and the incubating at block 310 complete in approximately the same amount of time or less time than the time it takes for a sample mixture to be processed in the imaging equipment and for the lines of the imaging equipment to be flushed and/or cleaned. In this way, a first sample mixture can be imaged while a second sample mixture is being combined and incubated. Once the first sample mixture has been imaged and the imaging equipment has been cleaned, the second sample mixture can immediately be imaged.

In alternate embodiments, the combining at block 308 and the incubating at block 310 complete in less than twice the time it takes for a sample mixture to be processed in the imaging equipment and for the lines of the imaging equipment to be flushed and/or cleaned. In this way, while a first sample mixture is being imaged, a second sample mixture can be ready to be imaged, and a third sample mixture and fourth sample mixture can be in the process of being combined and incubated. Once the first sample mixture has been imaged and the imaging equipment has been cleaned, the second sample mixture can immediately be imaged. The third sample mixture can be finishing its combining and incubating and the fourth sample mixture can still be combining and incubating. Once the second sample mixture has been imaged and the imaging equipment has been cleaned, the third sample mixture can immediately be imaged, while the fourth sample mixture begins to finish combining and incubating and a fifth sample mixture begins combining and incubating. The process can continue indefinitely to continually image sample mixtures.

Through non-trivial efforts and experimentation, it has been found that surprisingly effective results can be achieved through a combination of certain embodiments of the particle contrast agent composition 210, certain ways of combining the particle contrast agent composition 210 with the sample, and certain ways of incubating the sample mixture.

Specifically, surprisingly effective results can be achieved by using a particle contrast agent composition 210 including 90% pure or greater Crystal Violet at about 7.8 µM under staining conditions, 70% pure or greater New Methylene Blue at about 735 µM under staining conditions, 80% pure or greater Eosin-Y at about 27 µM under staining conditions, pre-treated saponin at about 50 mg/L to about 750 mg/L under staining conditions, and gluteraldehyde at about 0.1% or less under staining conditions; where the particle contrast agent 210 is combined with the sample at a ratio of particle contrast agent 210 to sample between about 3:1 and about 4:1; and where the resulting sample mixture is incubated at about 48° C. for about 45 seconds.

Certain effective particle contrast agent compositions 210 and staining procedures enable "Wright-like" stained images of vital and/or substantially intact cells to be efficaciously obtained with an automated visual analyzer using dyes in a non-alcohol based solvent system. Certain effective particle contrast agent compositions 210 and staining procedures enable rapid staining of samples such that various cellular components, nuclear lobes, and granular structures are clearly distinguishable. Certain effective particle contrast agent compositions 210 and staining procedures are suitable for supravital staining. Certain effective particle contrast agent compositions 210 and staining procedures are generate visual distinctions for particle categorization and subcategorization. Certain effective particle contrast agent compositions 210 and staining procedures are effective to enhance intracellular content features of particles in a serum, cerebrospinal fluid, pleural fluid, synovial fluid, seminal fluid, peritoneal fluid, amniotic fluid, lavage fluid, bone marrow aspirate fluid, effusions, exudates, or blood samples. Certain effective particle contrast agent compositions 210 and staining procedures are effective to stain neutrophils, lymphocytes, monocytes, eosinophils, basophils, platelets, reticulocytes, nucleated red blood cells, blasts, promyelocytes, myelocytes, metamyelocytes, casts, bacteria, epithelials, and/or parasites. Certain effective particle contrast agent compositions 210 and staining procedures are effective to generate visual distinctions for particle categorization and subcategorization, for example, by providing for differential staining of primary and secondary granules in cells, such as to aid in sub-categorization of immature granulocytes and their age determination based on the differential staining or enhancement of primary and secondary granules. Certain effective particle contrast agent compositions 210 and staining procedures are effective to generate visual distinctions for counting and characterizing red blood cells, reticulocytes, nucleated red blood cells, and platelets, as well as for white blood cell differential counting and white blood characterization and analysis. Certain effective particle contrast agent compositions 210 and staining procedures are effective to generate visual distinctions in vital and/or viable cells and/or cells with structures that remain substantially intact. Certain effective particle contrast agent compositions 210 and staining procedures are effective for staining subcellular structures of neutrophils, lymphocytes, monocytes, eosinophils, and basophils as well as reticulocytes, nucleated red blood cells, platelets, blast, promyelocyte, myelocyte, metamyelocyte, or cell fragments.

The rapid staining enabled by certain effective particle contrast agent compositions 210 and staining procedures described herein can be used with manual or semi-automated imaging and/or analysis procedures.

Through non-trivial efforts and experimentation, it has been found that surprisingly effective results can be achieved with certain embodiments of the particle contrast agent composition 210 comprising particle contrast agents in a non-alcohol based solvent system that are able, for the first time to the inventors' knowledge, to generate "Wright-like" stain images of vital and/or substantially intact cells which can reveal various cellular components, nuclear lobes, and granular structures, and make these particle and/or cellular features visually distinct.

Through non-trivial efforts and experimentation, it has been found that surprisingly effective results can be achieved when using a particle contrast agent composition 210 composed as listed in Table 1, where the Working Stain Reagent is made by mixing 40 mL of New Methyl Blue and 5 mL of Crystal Violet.

TABLE 1

| | |
|---|---|
| 50 mL | Phosphate Buffered Saline |
| 40 mL | Working Stain Reagent |
| 40 mL | 0.09% New Methyl Blue in CDS 5PD-Lytic |
| 5 mL | 0.009% Crystal Violet in CDS 5PD-Lytic |
| 10 mL | 0.5% Saponin |
| an amount sufficient to achieve 0.1% under staining conditions | Gluteraldehyde |

Figure 4:
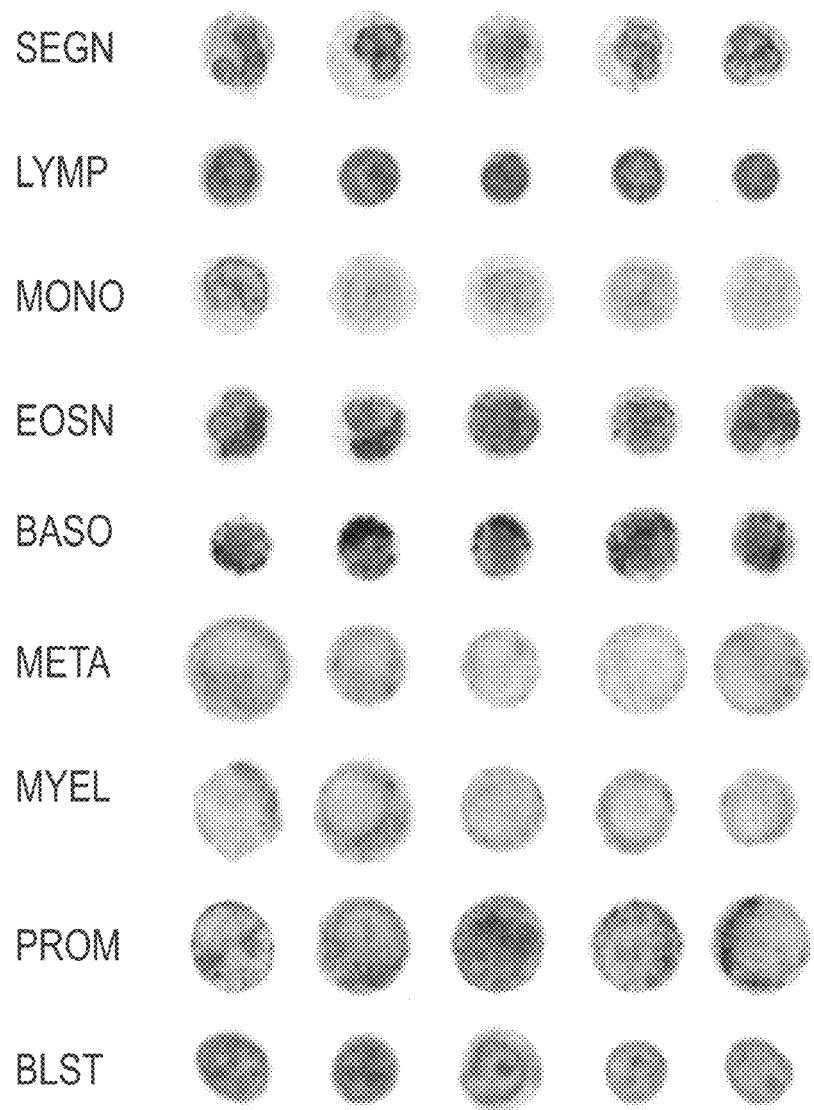
FIG. 4 is a representative illustration of selected white blood cells stained according to the rapid, one-step staining process according to one embodiment.

FIG. 4 is a representative illustration of selected white blood cells from a sample stained with the particle contrast agent composition 210 set forth in Table 1 and stained using the rapid, one-step staining procedures set forth above. The white blood cells are intact and show staining characteristics of a Wright stain. The various types of white blood cells (e.g., neutrophils, lymphocytes, monocytes, eosinophils, basophils, etc) are visually differentiable.

In some embodiments, features of cells stained by the particle contrast agent compositions of this disclosure are noted in Table 2.

TABLE 2

| Cell Type/Cell Substructure | Size (relative to RBC) | Shape | Color | Details |
|---|---|---|---|---|
| RBC | Standard | Round | | Central Pallor |
| Nucleated RBC | Standard | Round | Stained Nucleus | |
| NEUT | Large | Round to Oval | Nucleus Stained | Cytoplasmic Granules |
| NEUT: Nucleus | Interm. % | Segmented | Colored by Stain | Multiple Lobes |
| LYMP | Standard to small | Round to Ovoid | Nucleus Stained | Small Cytoplasm |
| LYMP: Nucleus | Large % | Round | Colored by Stain | Single Lobed |
| MONO | Large | Round | Nucleus Stained Lightly Colored cytoplasm | Large Cytoplasm |
| MONO: Nucleus | Interm % | Irregular | Colored by Stain | Nucleus Stains Light |
| EOS | Intermediate | Round | Stained Nucleus and Granules | Coarse large granules |
| EOS: Nucleus | Small to Interm. % | Segmented | Colored by Stain | Multiple Large Lobes |
| BASO | Standard to Small | Round | Nucleus and Granules stained | Coarse dense granules in Cytoplasm |
| BASO: Nucleus | Large % | Segmented | Colored by Stain | May be Obscured by Dark Granules |

In certain embodiments, the stain/dye composition is formulated for stability, ease of storage, disposal, and/or limited toxicity.

Figure 5:
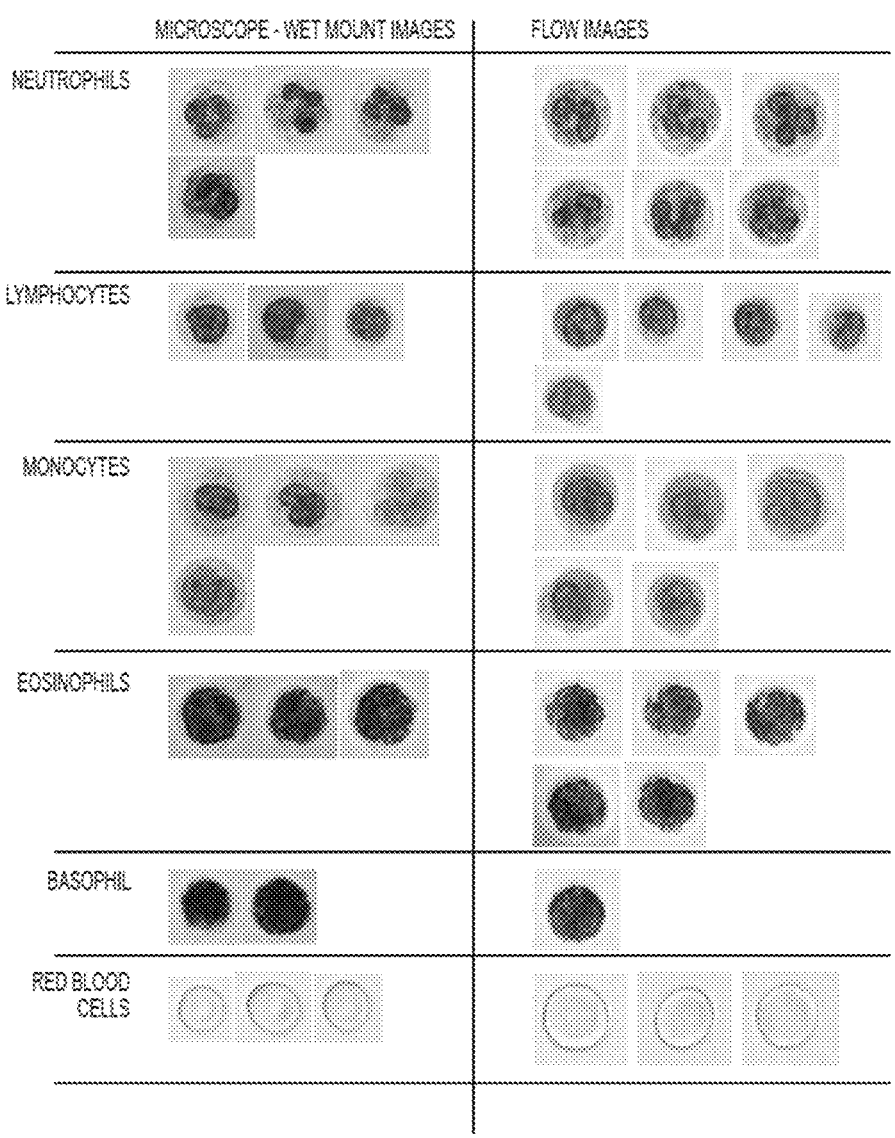
FIG. 5 is a representative illustration of selected while blood cells from a sample stained with a particle contrast agent composition according to one embodiment.

FIG. 5 is a representative illustration of selected white blood cells from a sample stained with the particle contrast agent composition 210 according to one embodiment, including cells imaged through manual, wet mount imaging and automatic flow imaging.

Early Experimentation

As described with reference to the examples below, numerous staining compositions and methods were tested and modified in order to result in the embodiments disclosed above.

Figure 6:
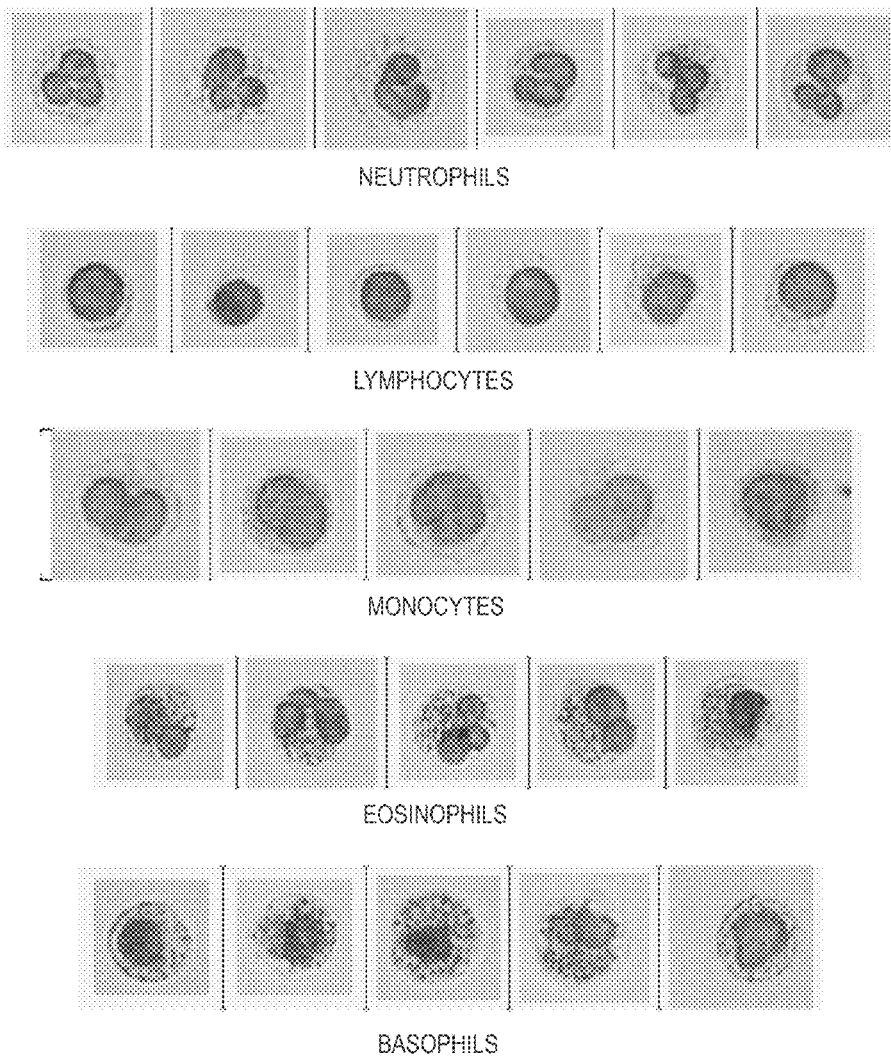
FIG. 6 is a representative illustration of stained cells according to an early Example 1.

In an early Example 1, a two-step staining method existed where a sample and an early embodiment of a particle contrast agent composition were combined and incubated for 40 seconds at 47.5° C., and then a quenching reagent was applied to the sample mixture. The particle contrast agent composition included Coulter LH Series Diluent, Coulter Lyse S III diff Lytic Reagent, Coulter LH Series Pak Reagent Kit, and Coulter LH Series RETIC PAK Reagent Kit. The results are seen in FIG. 6.

In an early Example 2 after Example 1, the two-step staining method of Example 1 was replaced by a one-step staining method. The improved results of Basophils are seen in FIG. 7 as compared to the results of Example 1.

In an early Example 3, a particle contrast agent composition without including gluteraldehyde resulted in weakened white blood cells that would break apart because of the shear forces in the flowcell. Images of the results of Example 3 showing damaged membranes are shown in FIG. 8.

In an early Example 4 after Example 3, gluteraldehyde was added to the particle contrast agent composition. The white blood cell membranes were more intact in Example 4, but the nucleus membranes were still damaged. After making adjustment to the PIOAL to reduce the glycerol content, the morphology of the white blood cells were mostly unchanged during imaging, as shown in FIG. 9.

In early examples with two-dye stains using particle contrast agent compositions of New Methylene Blue and Crystal Violet, most cell types were well distinguishable except for eosinophils, which were somewhat inconsistent and not always easy to distinguish from neutrophils, as shown in FIG. 10. In a subsequent Examples 5 and 6, a third particle contrast agent was added to the particle contrast agent composition.

In Example 5, Methyl Green was added to the particle contrast agent composition. The methyl green helped stain the eosinophils better, but the nucleus of the cells no longer stains with the desired purple, but blue. FIG. 11 depicts images of Example 5 neutrophils with blue-stained nuclei, but lost granular detail.

Figure 12:
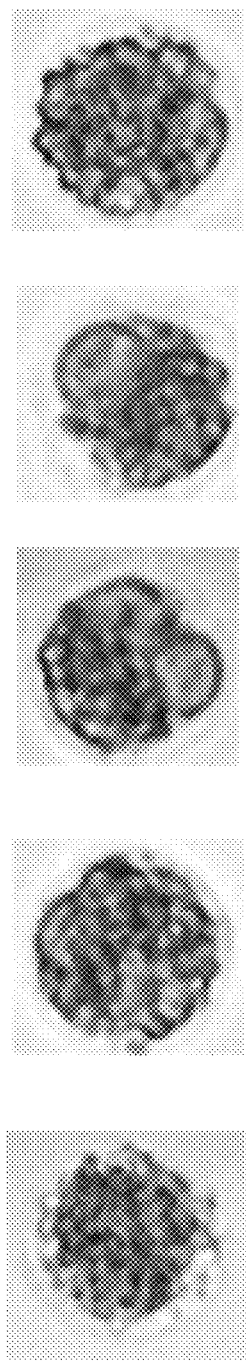
FIG. 12 is a representative illustration of stained cells according to an early Example 6.

In Example 6, Eosin-Y was used instead of Methyl Green as a third particle contrast agent in the particle contrast agent composition. The Eosin-y retained a purple stain of the nucleus and the granules stain consistently with a slightly orange shine, as seen in FIG. 12.

Through the experimentation mentioned above and additional experimentation, it has been determined that the disclosed embodiments and claimed embodiments provide preferential results.

All patents, patent publications, patent applications, journal articles, books, technical references, and the like discussed in the instant disclosure are incorporated herein by reference in their entirety for all purposes.

Any headers used herein are for organizational purposes only and are not to be construed to limit the disclosure or claims in any way.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention. Accordingly, the present invention is not limited to the embodiments described above or depicted in the drawings, and various embodiments and modifications can be made without departing from the scope of the claims below.

What is claimed is:

1. A particle contrast agent composition for staining a blood fluid sample being imaged in an automated particle analysis system comprising:
   at least one particle contrast agent selected from the group consisting of Crystal Violet, New Methylene Blue, Methyl Green, Eosin Y, and Safranin O;
   a permeabilizing agent including saponin present in amounts sufficient to result in concentrations between about 50 mg/L and about 750 mg/L under staining conditions; and
   a fixing agent including gluteraldehyde present in amounts sufficient to result in concentrations at or below 0.1% under staining conditions.

2. The composition of claim 1, wherein:
   the at least one particle contrast agent includes Crystal Violet, New Methylene Blue, and Eosin-Y;
   a ratio of the Crystal Violet to the New Methylene Blue is between about 1:90 to about 1:110 under staining conditions; and
   the Eosin-Y is present in amounts sufficient to result in concentrations of about 3 µM to about 300 µM under staining conditions.

3. The composition of claim 2, wherein:
   the Crystal Violet is present in amounts sufficient to result in concentrations of about 6 µM to about 10 µM under staining conditions;
   the New Methylene Blue is present in amounts sufficient to result in concentrations of about 70 µM to about 2.4 mM under staining conditions; and
   the Eosin-Y is present in amounts sufficient to result in concentrations of about 10 µM to about 50 µM under staining conditions.

4. The composition of claim 3, wherein:
   the Crystal Violet is approximately 90% pure or greater;
   the New Methylene Blue is approximately 70% pure or greater; and
   the Eosin-Y is approximately 80% pure or greater.

5. The composition of claim 4, wherein:
   the Crystal Violet is present in amounts sufficient to result in concentrations of about 7.8 µM under staining conditions;
   the New Methylene Blue is present in amounts sufficient to result in concentrations of about 735 µM under staining conditions; and
   the Eosin-Y is present in amounts sufficient to result in concentrations of about 27 µM under staining conditions.

6. The composition of claim 3, additionally comprising: buffer components.

7. A method of treating particles of a blood fluid sample which will be imaged using an automated particle analysis system comprising:
   combining the blood fluid sample with a particle contrast agent composition to obtain a sample mixture; and
   incubating the sample mixture at a temperature between about 37° Celsius and about 60° Celsius for fewer than 90 seconds;
   wherein the particle contrast agent composition includes:
   at least one particle contrast agent selected from the group consisting of Crystal Violet, New Methylene Blue, Methyl Green, Eosin Y, and Safranin O;
   a permeabilizing agent including saponin present in amounts sufficient to result in concentrations between about 50 mg/L and about 750 mg/L under staining conditions; and
   a fixing agent including gluteraldehyde present in amounts sufficient to result in concentrations at or below 0.1% under staining conditions.

8. A method of claim 7, wherein:
   the particle contrast agent composition includes Crystal Violet New Methylene Blue in amounts sufficient to result in a ratio of the Crystal Violet to the New Methylene Blue between about 1:1 to about 1:500 under staining conditions; and
   incubating the sample mixture includes heating the sample mixture fewer than 60 seconds.

9. The method of claim 8, wherein:
   the particle contrast agent composition includes:
   Crystal Violet present in amounts sufficient to result in concentrations at about 6 µM to about 10 µM under staining conditions;

New Methylene Blue present in amounts sufficient to result in concentrations of about 70 μM to about 2.4 mM under staining conditions; and Eosin-Y present in amounts sufficient to result in concentrations of about 10 μM to about 50 μM under staining conditions; and combining the blood fluid sample with the particle contrast agent composition includes combining to a ratio of the blood fluid sample to the particle contrast agent composition of about 1:2 to about 1:10.

10. The method of claim 8, wherein incubating the sample mixture includes heating the sample mixture to between about 46° C. and about 49° C. for between 40 and 50 seconds.

11. The method of claim 10, wherein:
the Crystal Violet is approximately 90% pure or greater;
the New Methylene Blue is approximately 70% pure or greater; and
the Eosin-Y is approximately 80% pure or greater.

12. The method of claim 10, wherein:
the particle contrast agent composition includes:
Crystal Violet present in amounts sufficient to result in concentrations at about 7.8 μM under staining conditions;
New Methylene Blue present in amounts sufficient to result in concentrations of about 735 μM under staining conditions;
Eosin-Y present in amounts sufficient to result in concentrations of about 27 μM under staining conditions; and
buffer components;
combining the blood fluid sample with the particle contrast agent composition includes combining to a ratio of the blood fluid sample to the particle contrast agent composition of about 1:3 to about 1:4; and
incubating the sample mixture includes heating the sample mixture to about 47° C. for about 45 seconds.

* * * * *